United States Patent [19]

Yamakawa

[11] Patent Number: 4,967,069
[45] Date of Patent: Oct. 30, 1990

[54] SPHERICAL PHOTOELECTRIC SENSOR

[76] Inventor: Masami Yamakawa, Kenei Hakuyoudai Apt. 14-301, Kashio-cho, Totsuka-ku, Yokohama-shi, Japan

[21] Appl. No.: 284,199

[22] Filed: Dec. 14, 1988

[30] Foreign Application Priority Data

Aug. 2, 1988 [JP] Japan .................................. 63-193301

[51] Int. Cl.$^5$ ............................................. G01B 21/00
[52] U.S. Cl. ..................................... 250/221; 350/620
[58] Field of Search .................. 356/218, 43; 350/416, 350/620; 250/221, 353; 340/556, 600

[56] References Cited

U.S. PATENT DOCUMENTS

| | | | |
|---|---|---|---|
| 3,064,526 | 11/1962 | Lindsay | 350/620 |
| 3,671,109 | 6/1972 | Sugano et al. | 350/620 |
| 3,679,906 | 7/1972 | Myers | 250/221 |
| 3,740,562 | 6/1973 | Fertig | 250/221 |
| 3,774,039 | 11/1973 | Price | 250/221 |
| 4,012,635 | 3/1977 | Walter et al. | 250/221 |
| 4,013,886 | 3/1977 | Schmid | 340/600 |
| 4,331,868 | 5/1982 | Mash | 250/221 |
| 4,664,515 | 5/1987 | Imura et al. | 356/43 |

FOREIGN PATENT DOCUMENTS 98381 6/1985 Japan .................................. 250/221

Primary Examiner—Richard A. Rosenberger
Attorney, Agent, or Firm—Morrison Law Firm

[57] ABSTRACT

A spherical photoelectric sensor comprising: a semispherical optical body including a light transmitting means having a light transmitting lens, and a light receiving lens means; and a semispherical electronic circuit block. The light transmitting means is formed in a recess of a semispherical transparent lens body and includes: a casing having a light emitting element on its bottom; and a light transmitting lens fitted in the casing and having a surface communicated with a surface of the transparent lens body. The light receiving lens means includes: the transparent lens body; a concave mirror formed at a rear side thereof; a convex mirror formed on an outer bottom of the casing to oppose to the concave mirror; and a light collecting lens formed on a center thereof. The light collected by the light receiving lens is received by the light receiving element in the electronic circuit block.

12 Claims, 4 Drawing Sheets

SPHERICAL PHOTOELECTRIC SENSOR

BACKGROUND OF THE INVENTION

1. Field of the Invention

This invention relates to a spherical photoelectric sensor for detecting a presence and vice versa of an object by irradiating an infrared light.

2. Description of the Prior Art

According to a conventional photoelectric sensor, a convex lens is disposed in a circular opening which is formed on a front wall of a box-shaped casing, and a light emitting element such as a light emitting diode or a light receiving element such as a phototransistor is positioned on a focal point of the convex lens. A lighting drive circuit, a signal amplifying circuit, a motion indicating lamp, a variable resistor and other components are all fixed on an internal wall of the box-shaped casing and electrically interconnected to each other, so that those components do not hinder light transmission from the convex lens up to the photoelectric sensor. The box-shaped casing is a closed type one, in which an electric wire is connected to both an input terminal and an output terminal.

FIGS. 4A and 4B show views of such a conventional photoelectric sensor, in which symbol A is a so-called reflective type photoelectric sensor comprising a light transmitting lens 2, a light receiving lens 3, a light emitting element 5, a light receiving element 6 and other electronic parts (not illustrated). Those components are all disposed in place within a box-shaped casing 1. Fixed on a side of the box-shaped casing 1 is a bracket 4 for regulating an optical axis. Numerals 4a and 4b respectively are a screw for regulating an optical axis.

Infrared light emitted from the light emitting element 5 is directed to a reflective mirror 7 through the light transmitting lens 2 as shown in FIG. 4B, and then the light is reflected upon the reflective mirror 7 and received by the light receiving element 6 through the light receiving lens 3. When an optical path of rays of light formed between the photoelectric sensor A and the reflective mirror 7 is shaded by an object 8 to be detected, the light receiving volume in the light receiving element 6 is varied, thereby variation of the light receiving volume is output as electric signals by the light receiving element 6. Thus, whether or not the object 8 to be detected is present in a detecting area can be detected.

In recent years, the structure of the photoelectric sensor has become more compact and more small-sized to respond to user's requirements. However, there exist two problems which hinder production of a compact photoelectric sensor.

Firstly, an assembly efficiency of the photoelectric sensor becomes lower as the structure of the photoelectric sensor casing becomes smaller. More specifically, when installing various electronic components on an inner wall of the casing, it is required to carry out such assembly by inserting a driver, pincers, a soldering iron and other tools into the interior of the casing. Accordingly, as the structure of the photoelectric sensor becomes smaller, the assembly work becomes more cumbersome.

Secondly, since the convex lens is employed to collect lights, a considerably broader space, i.e. a conical space is required for collecting the light toward the photoelectric element positioned on a focal point of the convex lens.

In other words, in order to enhance the performance of the photoelectric sensor, it is desirable to enlarge the diameter of the convex lens and increase the amount of the light collected. Thus, a focal distance of the convex lens becomes longer, whereby the effect of any outer disturbing light becomes less. Therefore, a convex lens having a larger diameter and a longer focal distance, as well as a broader conical space is needed.

As discussed above, a desire to make more compact the photoelectric sensor device is inconsistent with the betterment of its optical performance.

Thirdly, as shown in FIG. 4B, an optical axis of the infrared light emitted from the light transmitting lens 2 does not conform to an optical axis of the infrared light received by the light receiving lens 3, so that light receiving accuracy is decreased. Fourthly, it is cumbersome to regulate such an optical axes. As clearly shown in FIG. 4B, the disadvantage is that a plurality of screw have to be regulated exactly and speedily.

BRIEF SUMMARY OF THE INVENTION

It is therefore a general object of this invention to provide a spherical photoelectric sensor which is constructed compactly and enables accurate detection of the presence or absence of an object by irradiating an infrared light.

More specifically, the spherical photoelectric sensor comprises: a semispherical optical body including a light transmitting means having a light transmitting lens, and a light receiving lens means; and a semispherical electronic circuit block including a light receving element, a circuit substrate and electronic circuit parts.

The light transmitting means is formed in a recess of a semispherical transparent lens body and includes: a casing having a light emitting element on its bottom; and a light transmitting lens fitted in the casing and having a surface communicated with a surface of the semispherical transparent lens body.

The light receiving lens means includes: the semispherical transparent lens body; a concave mirror formed at an opposite side of an outer surface of said transparent lens body; a convex mirror formed on an outer bottom of the casing so as to oppose to the concave mirror; and a light collecting lens formed on a center of the concave mirror.

The light collected by the light collecting lens being received by the light receiving element in the electronic circuit block.

Under such structure, the outgoing light transmitted from the photoelectric sensor and the reflected light incoming thereinto are present in parallel with each other on their optical axes, so that the light receiving efficiency in the light receiving element is increased greatly and the detecting accuracy is also enhanced.

BRIEF DESCRIPTION OF THE ACCOMPANYING DRAWINGS

DETAILED DESCRIPTION OF PREFERRED EMBODIMENTS

Figure 1:
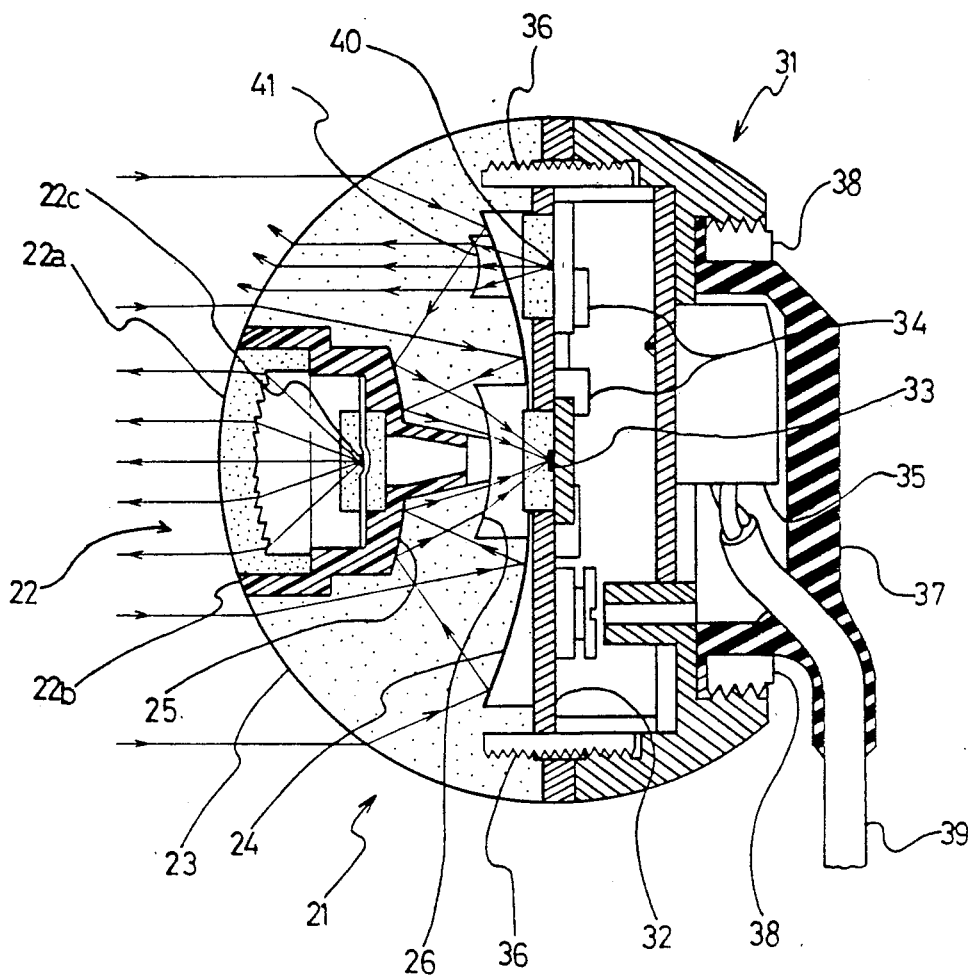
FIG. 1 is a partially cutaway section view of a photoelectric sensor according to an embodiment of this invention.

A preferred embodiment of this invention will now be described with reference to FIG. 1.

Numeral 21 is a semispherical optical block having a light transmitting means 22 and a light receiving means. The light transmitting means 22 comprises a light transmitting lens 22a and a light emitting element 22c disposed on a bottom of a casing 22b. The light transmitting means 22 is anchored within a semispherical transparent lens body 23 with the light emitting element 22c positioned upon a center axis of the transparent lens body 23. An outer surface of the light transmitting means 22a fitted in the casing 22b has the curved surface which is identical with a curvature of the transparent lens body 23. In this embodiment, the light transmitting lens 22a is a Fresnel one.

Numeral 24 is a concave mirror (a first mirror) formed on an opposite side of the outer surface of the semispherical transparent lens/23. Numeral 25 is a convex mirror (a second mirror) formed on an outer bottom of the casing 22b so as to face to the concave mirror 24. Numeral 26 is a light collecting lens, formed on a center of the concave mirror 24 so as to face to the convex mirror 25. The light receiving means comprises the transparent lens body 23, the concave mirror 24, the convex mirror 25 and the light collecting lens 26. Formed on the bottom of the casing 22b is an opening for wiring the light emitting element 22c.

Numeral 31 is a nearly semispherical electronic circuit block combined with the semispherical optical block 21, thereby a spherical photoelectric sensor is formed. Disposed in the electronic circuit block 31 are a circuit substrate 32, a light receiving element 33, various electronic parts 34, a connector 35 and the like. The light receiving element 33 is mounted on the circuit substrate 32 so as to face to the light collecting lens 26. Numeral 36 is a screw for fixing the optical block 21 with the electronic circuit block 31. Numeral 37 is a rubber-made cover for covering a rear opening of the electronic circuit block 31.

Numeral 38 is a stop screw for the cover 37, and numeral 39 is an electric wire for input and output. Numeral 40 is a light emitting element for motion indication which is disposed in the circuit substrate 32. The light of the light emitting element 40 is emitted to the exterior through a light collecting lens 41 and the transparent lens body 23, thereby an operating condition of the photoelectric sensor is indicated.

In this embodiment, the transparent lens body 23, the light transmitting lens 22a and the casing 22b are all made of a resinous material.

An operation of this embodiment will be described hereinafter.

When the light emitting element 22c is energized, the infrared light is, due to photoelectric conversion, irradiated to the exterior through the light transmitting lens 22a. The infrared light reflected by the reflective mirror or the object to be detected passes through the transparent lens body 23 and is reflected on the concave mirror 24. This is a first reflection. Then, the reflected light is received by the convex mirror 25 wherein a second reflection is made. Subsequently, the light is received by the light receiving element 33 through the light collecting lens 26.

Since the outgoing infrared light transmitted from the photoelectric sensor and the reflected light incoming thereinto are parallel and with each other on their optical axes are coaxial, a high light receiving efficiency is obtained.

As discussed above, an object may be detected by receiving the light reflected from that object. Alternatively, an object may be detected when the optical path between the reflective mirror and the photoelectric sensor is shaded by the object.

Figure 2:
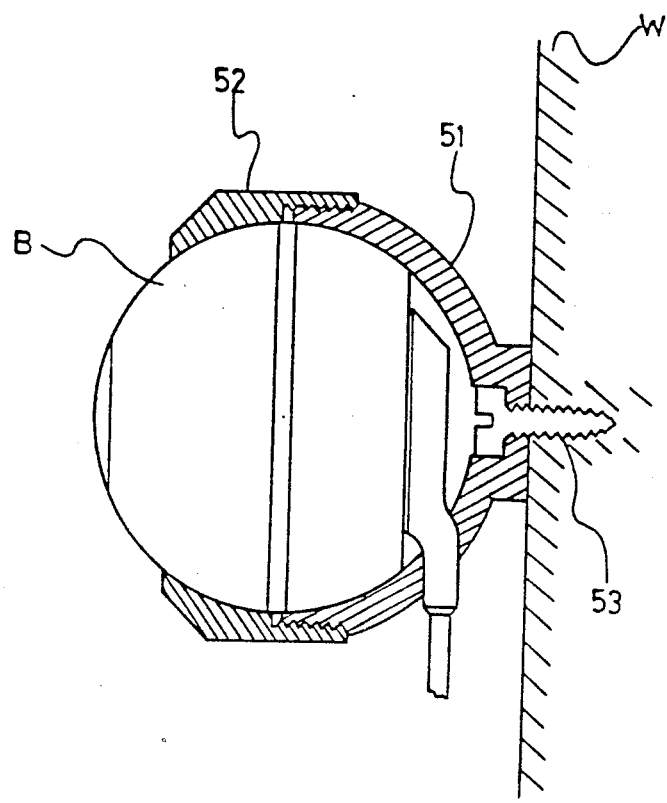
FIG. 2 is a schematic section view of an installation of a spherical photoelectric sensor according to this invention.
Figure 3:
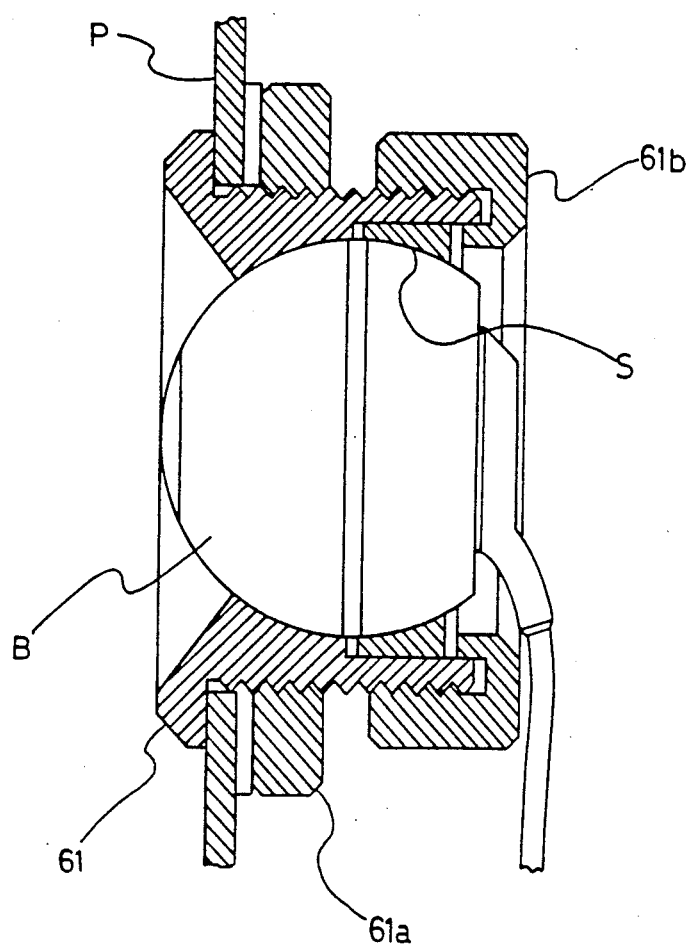
FIG. 3 is a schematic section view of another installation of the spherical photoelectric sensor in FIG. 2.
Figure 4A:
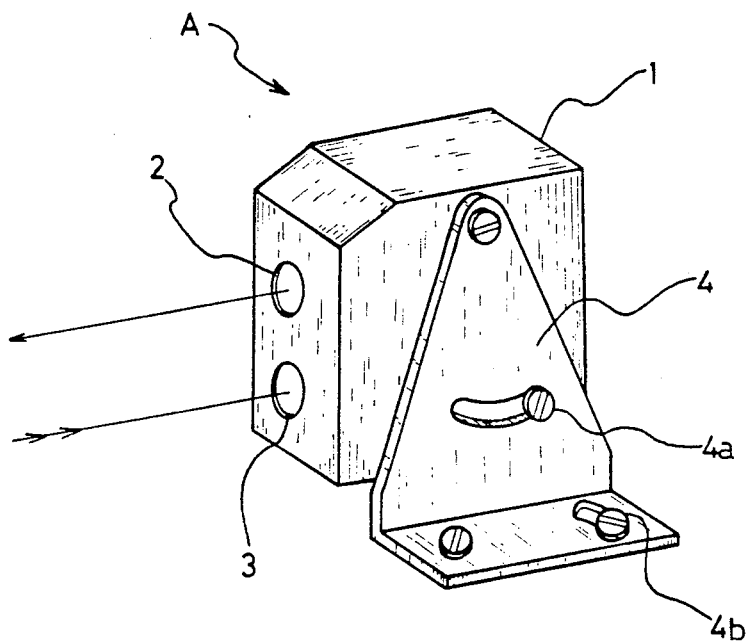
FIG. 4A is a perspective view of an outer appearance of a conventional photoelectric sensor.
Figure 4B:
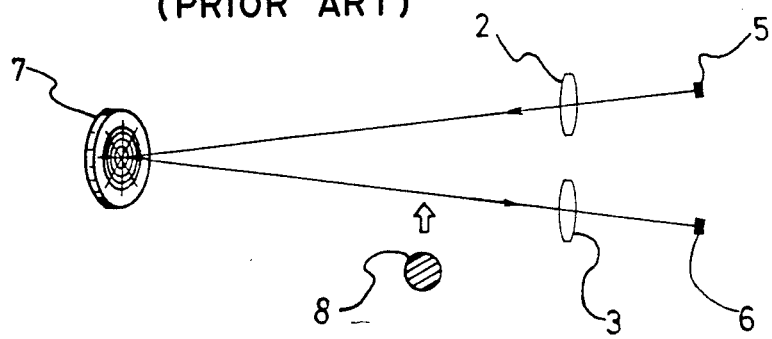
FIG. 4B is a view of an optical path in the conventional photoelectric sensor in FIG. 4A.

FIGS. 2 and 3 show schematic section views of installation of a spherical photoelectric sensor B according to this invention.

In FIG. 2, numeral 51 is a semispherical casing for supporting and holding the spherical photoelectric sensor B. The semispherical casing is fixed with a wall W by means of e.g. a screw 53. Numeral 52 is a ring-shaped casing for fixing a given direction of an optical axis of the photoelectric sensor B supported by the semispherical casing 51. As shown in FIG. 2, a threaded end of the ring-shaped casing 52 engages a threaded end of the semispherical casing 51. By loosening the ring-shaped casing 52, the photoelectric sensor B is rotatable freely within the semispherical casing 51, so that it is easy to set a preferred direction of the optical axis thereof exactly.

Referring to FIG. 3, symbol P is a panel for mounting the photoelectric sensor B thereupon. Numeral 61 is a casing for supporting and protecting the photoelectric sensor B. Numeral 61a is a screw for fixing the casing 61. Numeral 61b is a screw means for fixing the photoelectric sensor B. The screw means 61b can be engaged with a threaded portion of the casing 61. By loosening the screw means 61b, the photoelectric sensor B is rotatable freely within the casing 61, so that it is easy to set a preferred direction of the optical axis thereof exactly.

The effects of the present spherical photoelectric sensor can be summarized as follows:

(A) The outgoing infrared light transmitted from the spherical photoelectric sensor and the reflected light incoming thereinto are parallel and coaxial with each other, so that the light receiving efficiency in the light receiving element is increased greatly and the detecting accuracy is also enhanced. Whereas the detecting distance of a conventional reflective photoelectric sensor is 4 to 5 meters, it has been confirmed that that of the present photoelectric sensor is more than 10 meters.

(B) The present photoelectric sensor can be constructed compactly. For example, a diameter of the present photoelectric sensor having a detecting distance of more than 10 m can be set to about 26 mm.

(C) Since the effective area for receiving the reflected light in the present photoelectric sensor is much larger than that in the conventional photoelectric sensor, the improvement in detecting accuracy can be consistent with compactness of the spherical photoelectric sensor without contradition.

(D) Due to the spherical property of the present photoelectric sensor, it is easy to install it at any place a user wishes. For example, it is easy to slide the photoelectric sensor within the casing up-to-down or left-to-right, so that it is simple to regulate a direction to the detecting area accurately.

It is to be understood that the form of this invention shown and described is to be taken as a preferred embodiment of the same and that various modifications in the shape, size, arrangement of parts may be resorted to without departing from the spirit of this invention or the scope of the subjoined claims.

What is claimed is:

1. A spherical photoelectric sensor comprising: a semispherical optical body including a light transmitting means having a light transmitting lens, and a light receiving lens means; and a semispherical electronic circuit block including a light receiving element, a circuit substrate and electronic circuit parts;

said light transmitting means being formed in a recess of a semispherical transparent lens body and including: a casing having a light emitting element on its bottom; and a light transmitting lens fitted in said casing and having a surface communicated with a surface of said semispherical transparent lens body;

said light receiving lens means including: said semispherical transparent lens body; a concave mirror formed at an opposite side of an outer surface of said transparent lens body; a convex mirror formed on an outer bottom of said casing so as to oppose to said concave mirror; and a light collecting lens formed on a center of said concave mirror; and the light collected by said light collecting lens being received by said light receiving element in said electronic circuit block.

2. A spherical photoelectric sensor as claimed in claim 1, in which said light transmitting lens is a Fresnel lens.

3. A spherical photoelectric sensor as claimed in claim 1, including an indication lamp means for indicating a operating condition of said spherical photoelectric sensor.

4. A light receiving lens, comprising:
a single piece of transparent material;
an exterior surface of said single piece being a semispherical shape having an axis;
light being transmitted through said exterior surface into an interior of said single piece of transparent material;
a first concavity, concentric with said axis, at a rear surface of said transparent material;
said first concavity forming a first mirror;
said first mirror being effective to reflect said light entering said interior toward a front of said single piece;
a second concavity in a front of said single piece, concentric with said axis;
said second concavity forming a second mirror facing said first mirror;
said second mirror receiving said light reflected from said first mirror;
a third concavity in a rear surface of said single piece, concentric with said axis, and centered in said first mirror; and
said third concavity forming a collecting lens receiving said light reflected from said second mirror, whereby a three-element optical system is formed of said single piece.

5. A spherical photoelectric sensor, comprising:
a semispherical optical block;
first and second mirrors, facing each other, formed by first and second concavities concentrically formed in said optical block;
a collecting lens, facing said second mirror, formed by a third concavity, concentrically formed with said first and second concavities in said optical block;
a light transmitting element at a front surface of said optical block, disposed on an axis thereof;
said light transmitting element including means for transmitting light along said axis; and
means for receiving light collected by said collecting lens.

6. Apparatus according to claim 5, further comprising:
means for securing said semispherical optical block in a position;
said means for securing including an inner surface for contacting a semispherical surface of said optical block;
means for permitting rotation of said optical block within said means for securing, whereby said axis may be pointed in a desired direction; and
means for holding said axis in said desired direction.

7. Apparatus according to claim 6, wherein said means for securing further includes:
a first portion contacting a rear part of said semispherical optical block;
a second portion contacting a front portion of said semispherical optical block; and
means for clamping together said first and second portions, thereby capturing said optical block between them.

8. Apparatus according to claim 7, wherein said means for clamping includes threaded means for interconnecting said first and second portions.

9. A spherical photoelectric sensor comprising:
semispherical optical block;
said optical block including a transparent lens body made of a resinous material;
a concave portion in a front central part of said optical block;
a casing in said concave portion;
a first concave mirror integrally formed at a rear of said optical block;
a second convex mirror integrally formed in said optical block;
said second convex mirror facing said first concave mirror for receiving light reflected from said first concave mirror;
a light transmitting means in said casing;
a light collecting lens centered in said first concave mirror;
an electronic circuit block affixed to a rear of said optical block;
a light receiving element on said electronic circuit;
said light collecting lens directing light reflected from said second convex mirror to said light receiving element; and
said light transmitting means including a light transmitting lens in a center of said transparent lens body;
a light emitting element in said casing facing said light transmitting lens;
a curvature of said light transmitting lens being substantially identical to a curvature of said transparent lens body; and
said light transmitting lens being disposed at a level wherein its surface is generally continuous with a surface of said transparent lens body, whereby a forward portion of said sensor is substantially a portion of a sphere, 10. A spherical photoelectric sensor as claimed in claim 9, in which said light transmitting lens is a Fresnel lens.

11. A spherical photoelectric sensor as claimed in claim 9, further comprising:
   a second light emitting element;
   said second light emitting element being disposed at a rear of said transparent lens body; and
   a further lens for directing light from said second light emitting element outward through a front surface of said transparent lens body.

12. A spherical photoelectric sensor as claimed in claim 9, wherein:
   said electronic circuit block includes a semispherical outer surface;
   a curvature of said semispherical outer surface being substantially identical to a curvature of said semispherical optical block, and generally continuous therewith, whereby said semispherical optical block, said light transmitting lens, and said electronic circuit block, together, form said spherical photoelectric sensor.

* * * * *